(12) United States Patent
Smith et al.

(10) Patent No.: US 10,295,119 B2
(45) Date of Patent: May 21, 2019

(54) RUGGEDIZED HOUSING

(71) Applicant: Canrig Drilling Technology Ltd., Houston, TX (US)

(72) Inventors: Boone Elbert Smith, Pinehurst, TX (US); Jose Abelardo Sanchez, Katy, TX (US)

(73) Assignee: Canrig Drilling Technology Ltd., Houston, TX (US)

( * ) Notice: Subject to any disclaimer, the term of this patent is extended or adjusted under 35 U.S.C. 154(b) by 374 days.

(21) Appl. No.: 14/749,899

(22) Filed: Jun. 25, 2015

(65) Prior Publication Data
US 2015/0376987 A1    Dec. 31, 2015

Related U.S. Application Data

(60) Provisional application No. 62/019,035, filed on Jun. 30, 2014.

(51) Int. Cl.
*F16N 29/00*    (2006.01)
*G01N 33/28*    (2006.01)

(52) U.S. Cl.
CPC ......... *F16N 29/00* (2013.01); *G01N 33/2888* (2013.01); *F16N 2200/00* (2013.01)

(58) Field of Classification Search
CPC .. F16N 29/00; F16N 2200/00; F16N 2250/08; F16N 2250/36; G01N 33/2888
See application file for complete search history.

(56) References Cited

U.S. PATENT DOCUMENTS

| | | | |
|---|---|---|---|
| 2,650,796 A * | 9/1953 | Abraham | E21B 19/08 173/151 |
| 3,735,826 A * | 5/1973 | Constantinescu | E21B 10/24 175/228 |
| 4,334,862 A * | 6/1982 | Muckelrath | B65D 88/745 126/343.5 A |
| 4,733,556 A * | 3/1988 | Meitzler | B01D 27/08 340/631 |
| 5,274,335 A | 12/1993 | Wang et al. | |
| 5,726,622 A * | 3/1998 | Furuyama | G01N 27/126 338/35 |
| 5,750,887 A | 5/1998 | Schricker | |
| 6,268,737 B1 | 7/2001 | Marszalek | |
| 6,459,995 B1 | 10/2002 | Collister | |

(Continued)

FOREIGN PATENT DOCUMENTS

| | | |
|---|---|---|
| DE | 102008057842 A1 | 5/2010 |
| EP | 2535708 | 12/2012 |

OTHER PUBLICATIONS

Sensor Solutions, FPS2800612C4 Fluid Property Sensor, FPC012 Rev M, Sep. 2015, pp. 1-5.

(Continued)

*Primary Examiner* — Kipp C Wallace
(74) *Attorney, Agent, or Firm* — Abel Schillinger, LLP; Enrique Abarca

(57) ABSTRACT

A device for a drill rig comprising a ruggedized housing and a sensor contained in the ruggedized housing, the sensor adapted to measure at least one condition of a lubrication oil of an equipment on the drill rig. In an embodiment, the ruggedized housing can have a Class I, Division 1 & 2 standard rating according to UL1203 & FM3600(3615).

20 Claims, 6 Drawing Sheets

(56) References Cited

U.S. PATENT DOCUMENTS

| | | | |
|---|---|---|---|
| 6,553,812 B2* | 4/2003 | Park | G01N 11/08 |
| | | | 324/663 |
| 6,718,819 B2 | 4/2004 | Schoess | |
| 7,219,536 B2 | 5/2007 | Liu et al. | |
| 7,287,431 B2 | 10/2007 | Liu et al. | |
| 7,317,989 B2 | 1/2008 | DiFoggio et al. | |
| 8,166,803 B2 | 5/2012 | Haller et al. | |
| 8,280,639 B2 | 10/2012 | Conquergood | |
| 8,340,928 B2 | 12/2012 | Sun | |
| 8,370,009 B2 | 2/2013 | Gremminger et al. | |
| 8,387,720 B1 | 3/2013 | Keast | |
| 8,464,576 B2 | 6/2013 | Okuyama et al. | |
| 8,614,588 B2 | 12/2013 | Hedges | |
| 2004/0217879 A1* | 11/2004 | Guggari | E21B 47/18 |
| | | | 340/853.3 |
| 2005/0029125 A1* | 2/2005 | Jiang | G01N 27/403 |
| | | | 205/775 |
| 2007/0193776 A1* | 8/2007 | Luling | E21B 47/08 |
| | | | 175/6 |
| 2009/0206218 A1* | 8/2009 | Massey | B60B 7/02 |
| | | | 248/220.21 |
| 2010/0294383 A1* | 11/2010 | Melbo | E21B 33/0355 |
| | | | 137/551 |
| 2011/0231099 A1* | 9/2011 | Elkins | B09B 1/00 |
| | | | 702/12 |
| 2014/0265580 A1* | 9/2014 | Cooley | E21B 41/0085 |
| | | | 307/47 |
| 2015/0083436 A1* | 3/2015 | Wells | E21B 29/04 |
| | | | 166/376 |
| 2015/0129307 A1* | 5/2015 | Pope | E21B 47/01 |
| | | | 175/40 |
| 2015/0221572 A1* | 8/2015 | Chan | H01L 23/3107 |
| | | | 257/734 |
| 2016/0025265 A1 | 1/2016 | Smith et al. | |
| 2016/0054292 A1* | 2/2016 | O'Donnell | G01N 25/00 |
| | | | 702/22 |
| 2017/0030149 A1* | 2/2017 | Kadam | E21B 4/003 |
| 2017/0114957 A1* | 4/2017 | Conley | F16N 29/02 |
| 2017/0328196 A1* | 11/2017 | Shi | E21B 47/06 |

OTHER PUBLICATIONS

Fluid Property Sensors, Catalog SS-TS-TE100, Sep. 2016, pp. 24-27.
adalet.com, XIHS-chart-256, downloaded Nov. 14, 2017 pp. 1-2.
Explosionproof Instrument Housing XIH (Standard) Series, The ADALET Engineering Department, Adalet.com, 2 pages.

* cited by examiner

RUGGEDIZED HOUSING

CROSS-REFERENCE TO RELATED APPLICATION(S)

This application claims priority under 35 U.S.C. § 119(e) to U.S. Patent Application No. 62/019,035, entitled "RUGGEDIZED HOUSING," by Boone Elbert Smith and Jose Abelardo Sanchez, filed Jun. 30, 2015, which is assigned to the current assignee hereof and incorporated herein by reference in its entirety

FIELD OF THE DISCLOSURE

The present invention relates generally to a system for measuring at least one condition of a lubrication oil, and more particularly to a ruggedized system for measuring at least one condition of the lubrication oil.

RELATED ART

Drilling subterranean wells for oil and gas is expensive and time consuming. Formations containing oil and gas are typically located thousands of feet below the earth's surface. To access the oil and gas, thousands of feet of rock and other geological formations must be removed. To ensure a cost-effective drilling operation, equipment utilized in wellbore drilling operations must be capable of repeated, reliable operation even when subjected to extreme environmental conditions. Repair or replacement of failed equipment can shut down a drilling operation entirely, rendering the operation economically unsustainable.

Several of the equipment on a drill rig utilize lubrication oil. Ingress of contaminant(s), e.g., mud, sand, metal particles, water, and other non-oil fluids, into the lubrication oil can mitigate the bearing properties thereof, increasing frictional resistance and accelerating wear and ultimate failure of the equipment.

One or more sensors can be used to actively measure one or more of the conditions of the lubrication oil, but such sensors are limited in the environment of a drilling operation. Thus, a ruggedized device is proposed.

BRIEF DESCRIPTION OF THE DRAWINGS

Embodiments are illustrated by way of example and are not limited in the accompanying figures.

DETAILED DESCRIPTION

Figure 1:
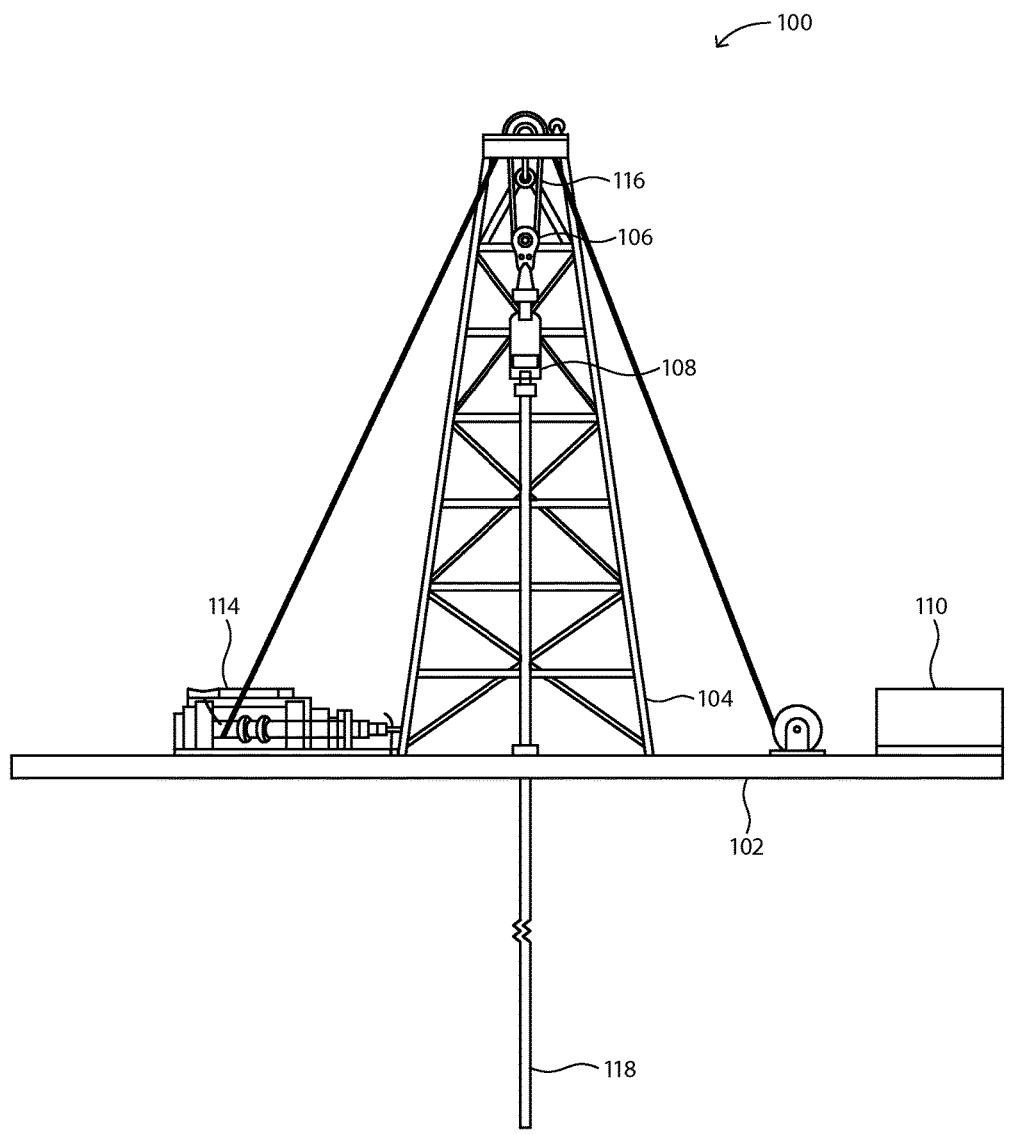
FIG. 1 includes a schematic view of a drill rig in accordance with an embodiment.

The following description in combination with the figures is provided to assist in understanding the teachings disclosed herein. The following discussion will focus on specific implementations and embodiments of the teachings. This focus is provided to assist in describing the teachings and should not be interpreted as a limitation on the scope or applicability of the teachings. However, other embodiments can be used based on the teachings as disclosed in this application.

The terms "comprises," "comprising," "includes," "including," "has," "having" or any other variation thereof, are intended to cover a non-exclusive inclusion. For example, a method, article, or apparatus that comprises a list of features is not necessarily limited only to those features but may include other features not expressly listed or inherent to such method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" is employed to describe elements and components described herein. This is done merely for convenience and to give a general sense of the scope of the invention. This description should be read to include one, at least one, or the singular as also including the plural, or vice versa, unless it is clear that it is meant otherwise. For example, when a single item is described herein, more than one item may be used in place of a single item. Similarly, where more than one item is described herein, a single item may be substituted for that more than one item.

Unless otherwise defined, all technical and scientific terms used herein have the same meaning as commonly understood by one of ordinary skill in the art to which this invention belongs. The materials, methods, and examples are illustrative only and not intended to be limiting. To the extent not described herein, many details regarding specific materials and processing acts are conventional and may be found in textbooks and other sources within the drilling and fluid sensing arts. Reference to standards, including UL standards, is intended to refer to those standards in effective practice at the time of filing.

The concepts are better understood in view of the embodiments described below that illustrate and do not limit the scope of the present invention. The following description is directed to a device for a drill rig including a ruggedized housing and a sensor contained in the ruggedized housing. The sensor can be adapted to measure at least one condition of a lubrication oil of an equipment on the drill rig. In accordance with one or more embodiments, the ruggedized housing can reduce or eliminate the transmission of harsh environmental conditions, e.g., acute impact, vibration, heat or fire, water, or any combination thereof, from the drill rig environment to the sensor.

Referring initially to FIG. 1, a drilling rig 100 can generally include a substructure 102 and a derrick 104. The derrick 104 can attach to the substructure 102 and can extend therefrom. The derrick 104 can be a tower or a guyed mast such as a pole which can be hinged at a bottom end. The derrick 104 and substructure 102 can be permanent or can be adapted to break down for transportation.

The drilling rig 100 can be an offshore drilling rig or a land based drilling rig. Offshore drilling rigs can take many forms. For example, the drilling rig 100 can have a fixed platform or substructure attached to an underlying seabed. Alternatively, the drilling rig 100 can include a floating platform disposed at least partially underwater with an anchoring system holding the drilling rig 100 relatively near the underwater drilling operation. It should be understood that the particular configuration and embodiment of the drilling rig 100 are not intended to limit the scope of the present disclosure.

In particular embodiments, the drilling rig 100 can further include a hoisting system 106, a rotating system 108, and a power supply 110. The derrick 104 can support the hoisting system 106 and the rotating system 108. In a particular embodiment, the hoisting system 106 can include a drawworks 114 and a block and tackle system 116 adapted to support a drill string 118.

In a particular aspect, at least one fluid measuring sensor can be disposed on, or adjacent to, an equipment of the drilling rig 100 to actively sense, measure, and generate data regarding a condition of a lubrication oil disposed in the equipment. The sensor can be adapted to detect a viscosity, density, dielectric, temperature, or any combination thereof of the lubrication oil. As used herein, "actively sense" refers to an act of sensing where a sensing condition occurs at least once every hour, at least once every 30 minutes, at least once every minute, or at least once every 10 seconds. In a particular embodiment, "actively sense" can refer to an act of sensing wherein a sensing condition occurs at least 1 time per minute (TPM), at least 30 TPM, at least 60 TPM, at least 120 TPM, or at least 300 TPM. Moreover, in particular embodiments, the sensors can sense the condition no greater than 5,000 TPM, no greater than 4,000 TPM, no greater than 3,000 TPM, no greater than 1,000 TPM, no greater than 500 TPM, or no greater than 300 TPM.

In an embodiment, the lubrication oil can be heavy weight lubrication oil. As used herein, "heavy weight lubrication oil" refers to a viscous lubricating oil adapted for use in equipment, such as, for example, gears, transmissions, transfer cases, differentials, and other similar machinery. More particularly, "heavy weight lubrication oil" can refer to a lubrication oil having a weight, as measured according to the Society of Automotive Engineers (SAE) of at least 75 W, at least 80 W, at least 85 W, at least 90 W, at least 140 W, or at least 250 W. Such heavy weight lubrication oils have a higher viscosity than conventional motor oil and are traditionally utilized in heavy machinery for their lubrication properties under high operational pressures and loads.

As contemplated herein, the sensors can be in fluid communication with oil pans and lubrication systems of equipment of the drill rig 100 that require lubrication oil. For example, the sensors can be disposed on the rotating system 108, e.g., a top drive, the draw works 114, the power supply 110, a transmission associated with any of the listed equipment, or any other similar heavy machinery equipment disposed on the drill rig 100.

In a certain embodiment, a single sensor can be disposed on the equipment. The sensor can be in fluid communication with the equipment by way of a fluid passageway extending from the equipment to the sensor. In a further embodiment, a plurality of sensors can be disposed on, such as directly on, the equipment. In an embodiment, the sensor may be disposed on an outer surface of the equipment. Because the lubrication oil may have different discernable conditions at different physical locations within the equipment, each of the plurality of sensors can be positioned on, or coupled to, different locations within, or on, the equipment. The measured data from each sensor can be individually monitored or, alternatively, can be averaged with the sensed data from all of the plurality of sensors to generate an average sensed condition value.

Drill rigs 100 can be dangerous environments for fragile or delicate equipment. Sensors and other electronics may be impacted by moving or falling tubulars; equipment secured to the derrick 104 can become lose and fall; blowouts or explosions can radiate shockwaves subjecting equipment to high forces; heat caused by explosions or fires can damage electronic components; and other generally impactful collisions can occur along the equipment, all of which can damage or destroy a fragile or delicate equipment.

Figure 2:
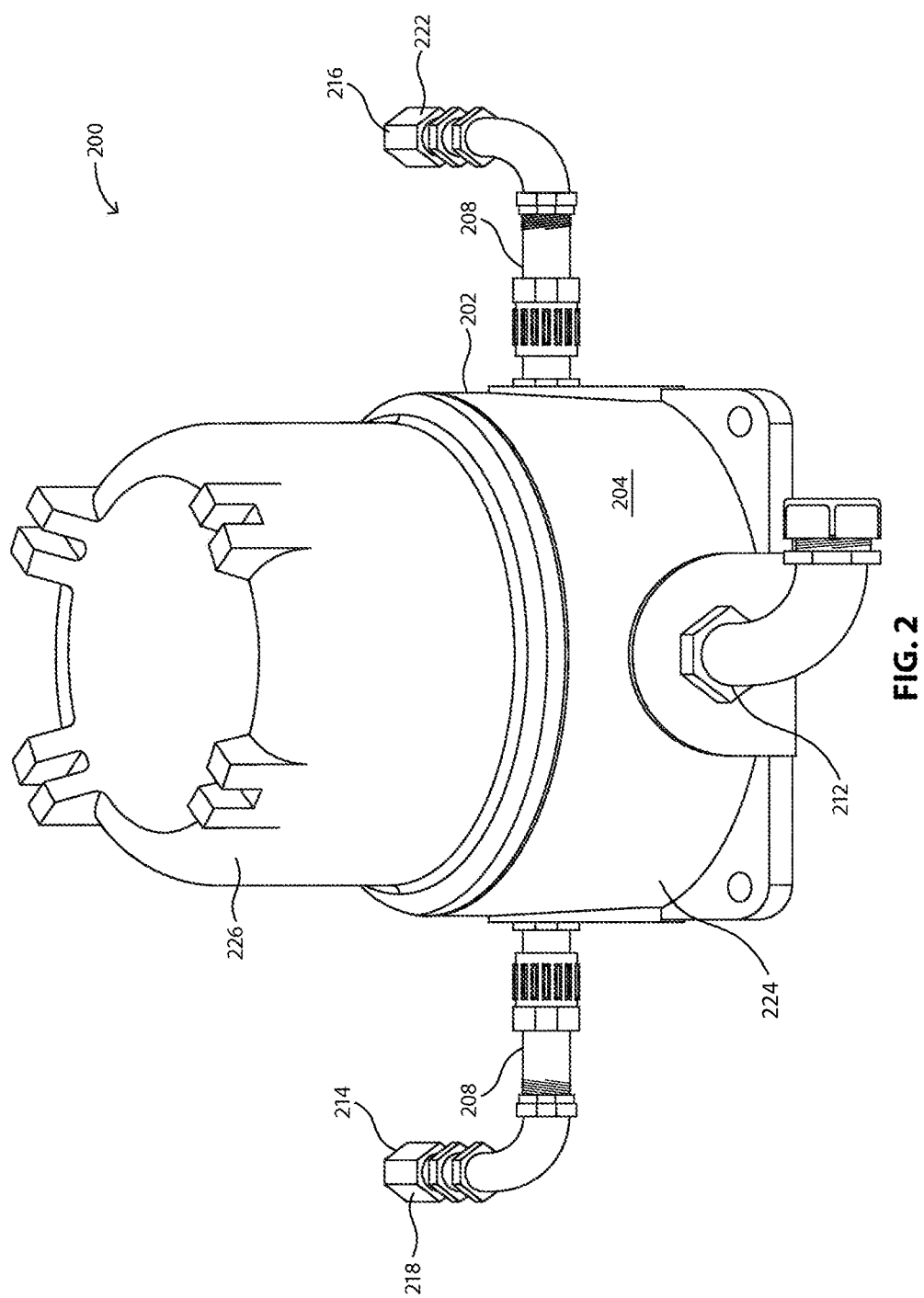
FIG. 2 includes a side perspective view of a ruggedized housing in accordance with an embodiment.
Figure 3:
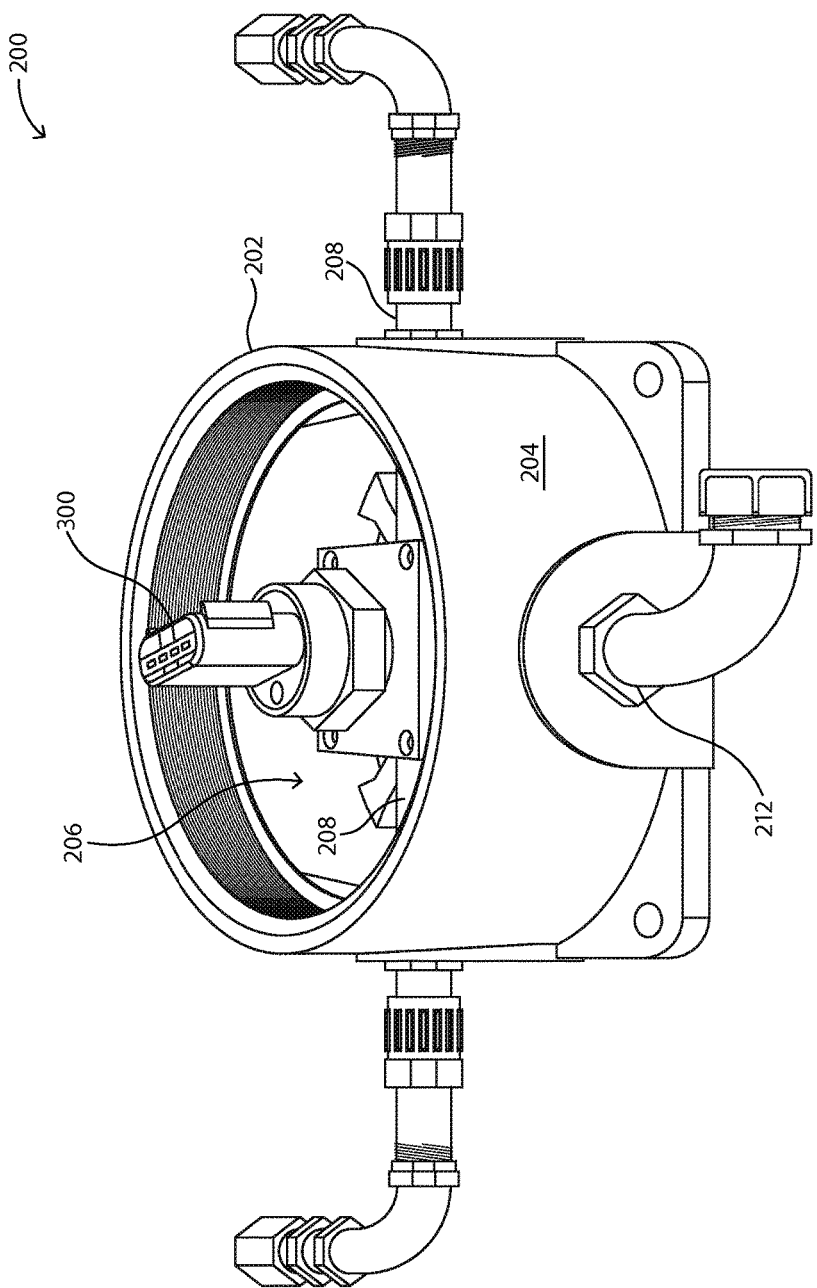
FIG. 3 includes a side perspective view of a ruggedized housing without a top in accordance with an embodiment.
Figure 4:
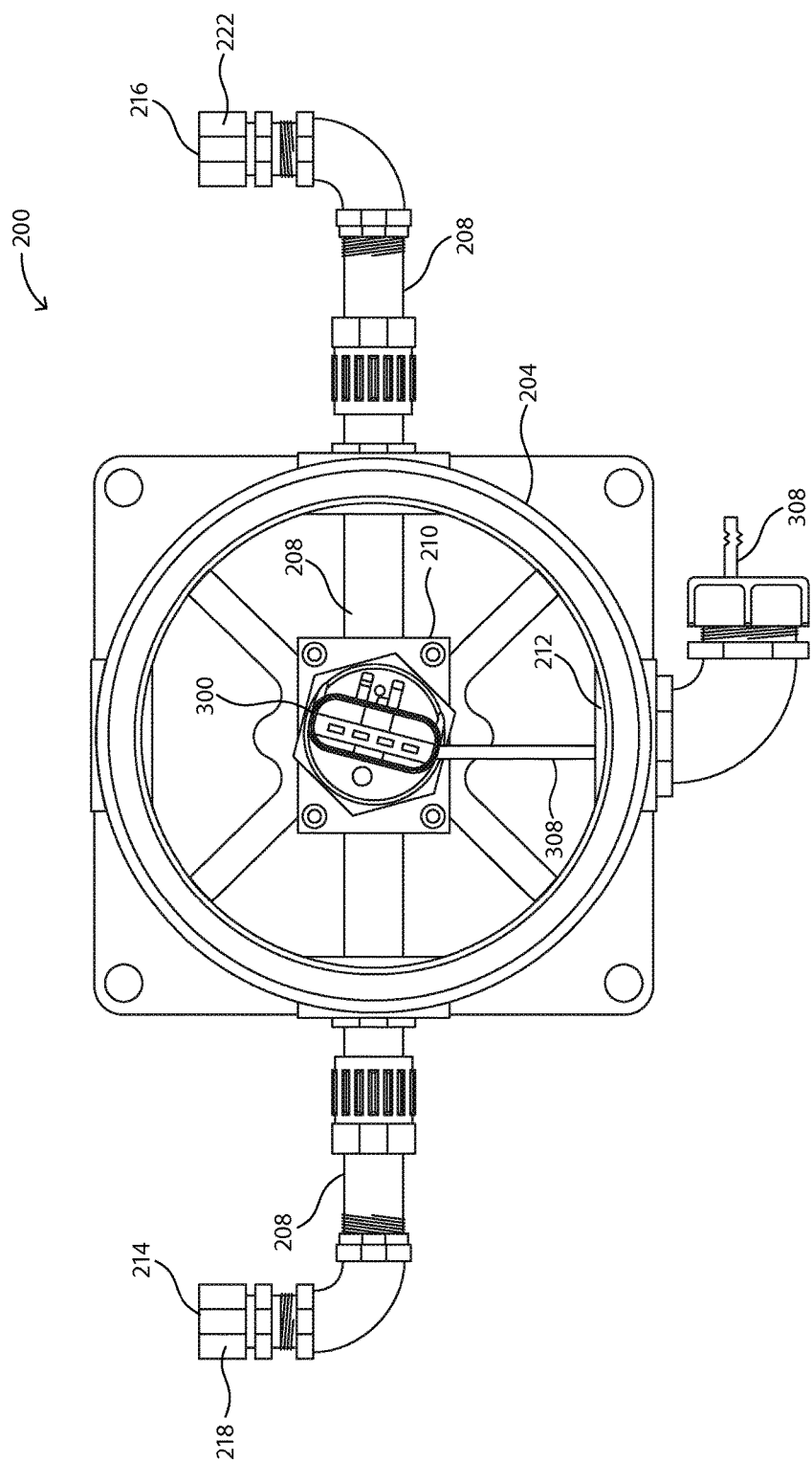
FIG. 4 includes a top elevation view of a ruggedized housing without a top in accordance with an embodiment.

Referring now to FIGS. 2 through 4, a ruggedized housing 200 may be used to protect a fragile or otherwise delicate equipment, such as, for example, a fluid monitoring sensor 300, from harsh environmental conditions. In an embodiment, the ruggedized housing 200 may protect the sensor 300, for example, from acute impact, vibration, heat or fire, water, or any combination thereof. The ruggedized housing 200 can generally include a body 202 having a wall 204 defining an internal volume 206.

In an embodiment, such as, for example, illustrated in FIG. 2, the ruggedized housing 200 can include a first component 224 and a second component 226, e.g., a first and a second half. The first and second components 224 and 226 can be removably engageable with one another. For example, in an embodiment, the first and second components 224 and 226 can be threadedly engageable. In such a manner, the internal volume 206 of the ruggedized housing 200 and the sensor 300 can be readily accessed by a user. In another embodiment, the first and second components 224 and 226 can be attached together, for example, by a bayonet connection, a threaded or non-threaded fastener, or another suitable connection element. Unlike a solid container, the use of first and second components 224 and 226 may allow for rapid replacement and repair of the sensor 300, which in turn may reduce downtime of the drill rig 100.

Figure 6:
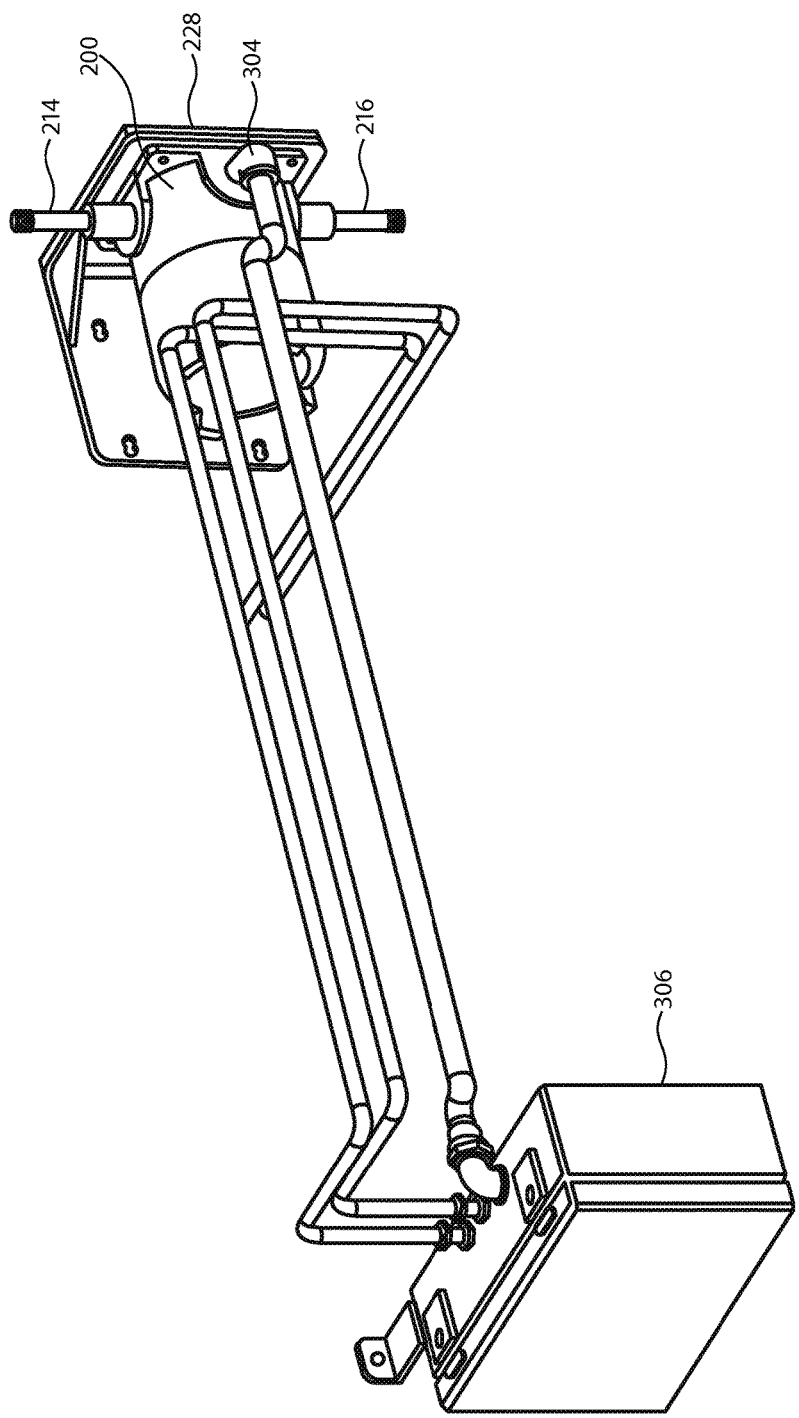
FIG. 6 includes a side perspective view of an assembly in accordance with an embodiment.

In a particular embodiment, the ruggedized housing 200 may have a Class I, Division 1 & 2 standard rating according to UL1203 & FM3600(3615). In such a manner, the ruggedized housing 200 can withstand or reduce the impact of an impact or explosion, and can reduce the transmission of damaging environmental conditions, such as shock waves, to the sensor 300. As illustrated in FIG. 6, a dampening element 228 can be disposed between the ruggedized housing 200 and the equipment. In an embodiment, the dampening element 228 can reduce transmission of shock or vibration from the equipment to the sensor 300. In a particular embodiment, the dampening element 228 may include a material, such as a polymeric material. The dampening element 228 may have a thickness between 0.1 cm and 100 cm, between 1 cm and 25 cm, or between 2 cm and 10 cm.

In accordance with one or more embodiments, the ruggedized housing 200 can allow the sensor 300 to withstand forces of at least 1 g-force, such as at least 5 g-force, at least 10 g-force, at least 25 g-force, at least 50 g-force, or even at least 75 g-force. That is, the ruggedized housing 200 may prevent or reduce transmission of such forces to the sensor 300. In such a manner, the ruggedized housing 200 may be rated to protect the sensor 300 from impacts or other force transmissions.

Referring again to FIGS. 2 through 4, a fluid passageway 208 can extend at least partially through the internal volume 206 of the ruggedized housing 200. The fluid passageway 208 can deliver lubrication oil from the equipment being monitored to the sensor 300. In a particular embodiment, the fluid passageway 208 can extend entirely through the internal volume 206 of the ruggedized housing 200. In a more particular embodiment, the fluid passageway 208 can extend between diametrically opposite locations of the wall 204 of the ruggedized housing 200. In an embodiment, the fluid passageway 208 can extend through the wall 204 of the ruggedized housing 200 at one or more locations. For example, the fluid passageway 208 can extend through the wall 204 at a first location and at a second location, the first and second locations being diametrically opposite each other.

In an embodiment, the fluid passageway 208 can lie along a straight, or substantially straight, line at locations inside the internal volume 206, such that the fluid passageway 208 defines a linear or substantially linear pathway through at internal volume 206. As used herein, "substantially straight" refers to a line that deviates from a straight line along a measured length by less than 20°, such as by less than 15°, by less than 10°, or even by less than 5°. A straight, or generally straight, fluid passageway 208 can reduce the formation of stress risers within the fluid passageway 208, create a laminar fluid flow, reduce aspiration of a fluid within the fluid passageway, mitigate the occurrence of fluid harmonic interactions, reduce wear of the fluid flow passageway, permit more accurate fluid property sensing conditions, or provide other similar benefits, which may facilitate improved accuracy of the sensor. Additionally, a straight, or generally straight, fluid passageway 208 may reduce the manufacturing complexities and weight of the ruggedized housing 200. In a particular embodiment, the fluid passageway 208 may be secured to the wall 204 of the ruggedized housing 200, such as, for example, by an adhesive, a weld, a threaded or non-threaded fastener, a mechanical hook or loop, any similar device, or any combination thereof. A fillet may extend around at least a portion of the fluid passageway 208 along a surface of the wall 204. The fillet may reduce stress concentration in the wall 204 or fluid passageway 208. This may increase operable lifespan of the ruggedized housing 200 or fluid passageway 208.

In an embodiment, the fluid passageway can be adjacent to the ruggedized housing. More particularly, the fluid passageway can be immediately adjacent to the ruggedized housing. In this regard, the sensor can be partially disposed within the ruggedized housing while sensing a condition of the lubrication oil disposed in the fluid passageway at a location external, or partially external, to the ruggedized housing.

The fluid passageway 208 can define opposing distal ends 214 and 216. In an embodiment, each distal end 214 and 216 can be disposed at a location outside of the ruggedized housing 200. In a particular embodiment, the distal end 214 can include an engagement element 218 adapted to engage the fluid passageway 208 with an inlet line extending from the equipment being monitored. The engagement element 218 can include, for example, a component having a threaded portion (e.g., a rotatable collar including a threaded surface), a ball locking system (e.g., a component having a collar, a race, and one or more ball bearings), a bayonet connection, any other suitable engagement element, or any combination thereof. The inlet line can terminate in a mating engagement element, permitting an operator to attach the inlet line to the engagement element 218.

In a similar manner, the distal end 216 can include an engagement element 222 adapted to engage the fluid passageway 208 with an outlet line extending to the equipment being monitored. Similar to the engagement element 218, the engagement element 222 can include, for example, a component having a threaded portion (e.g., a rotatable collar including a threaded surface), a ball locking system (e.g., a component having a collar, a race, and one or more ball bearings), a bayonet connection, any other suitable engagement element, or any combination thereof. The outlet line can terminate in a mating engagement element, permitting an operator to attach the outlet line to the engagement element 222. In such a manner, lubrication oil can be drawn from the equipment, passed through the ruggedized housing 200, measured by the sensor 300, and returned to the equipment in a single flow direction.

In a more particular embodiment, the fluid passageway 208 or the ruggedized housing 200 can further include a fluid urging component (not illustrated) adapted to circulate the lubrication oil through the fluid passageway 208. In an embodiment, the fluid urging component can include a pump or fluid circulator.

In another embodiment, the fluid passageway can extend from the equipment to the sensor within the ruggedized housing. In this embodiment the fluid passageway can have a bidirectional flow path. In such a manner, fluid can pass through the fluid passageway in both directions, permitting the sensor to passively measure the conditions of the lubrication oil without a continuous active flow. As used herein, "passively measure" refers to a condition whereby lubrication oil is not urged past the sensor, but rather, the sensor is in fluid communication with the equipment and is adapted to sense the condition of the lubrication oil without a constant flow rate of lubrication oil.

In an embodiment, the sensor 300 can be attached to the fluid passageway 208. The sensor 300 can be adapted to receive and measure a condition of unfiltered lubrication oil. As used herein, "unfiltered lubrication oil" refers to lubrication oil which has not yet been filtered or otherwise screened, cleansed, or altered by a mechanism, process, or method, such as, for example, by a filter, a screen, a chemical reaction, or any combination thereof. The measurement of unfiltered lubrication oil may better detect the condition of the lubrication oil as contained within the equipment. For example, screening the lubrication oil through a filter may remove microscopic metal flakes or scrapings which may indicate impending equipment failure. Positioning the filter along the fluid passageway 208 at a location prior to the sensor 300, such that the lubrication oil first passes through the filter prior to the sensor, may prevent the sensor from detecting the metal flakes or scrapings.

In an embodiment, the sensor 300 can be removeably engaged with the fluid passageway 208. In such a manner, the sensor 300 can be readily replaced, cleaned, or adjusted by an operator. In a particular embodiment, the sensor 300 can be threadedly engaged to the fluid passageway 208. In other embodiments, the sensor 300 can be engaged to the fluid passageway 208 by another suitable method for fastening two objects together, such as, for example, by an adhesive, a threaded or non-threaded fastener, mechanical deformation (e.g., crimping) of one or both of a portion of the body and a portion of the sensor, a bayonet connection, an interference fit, a loaded ball bearing race, a cotter pin, a pin or tab engagement, or any combination thereof. The scope of the disclosure is not intended to be limited by those fastening methods described above.

Figure 5:
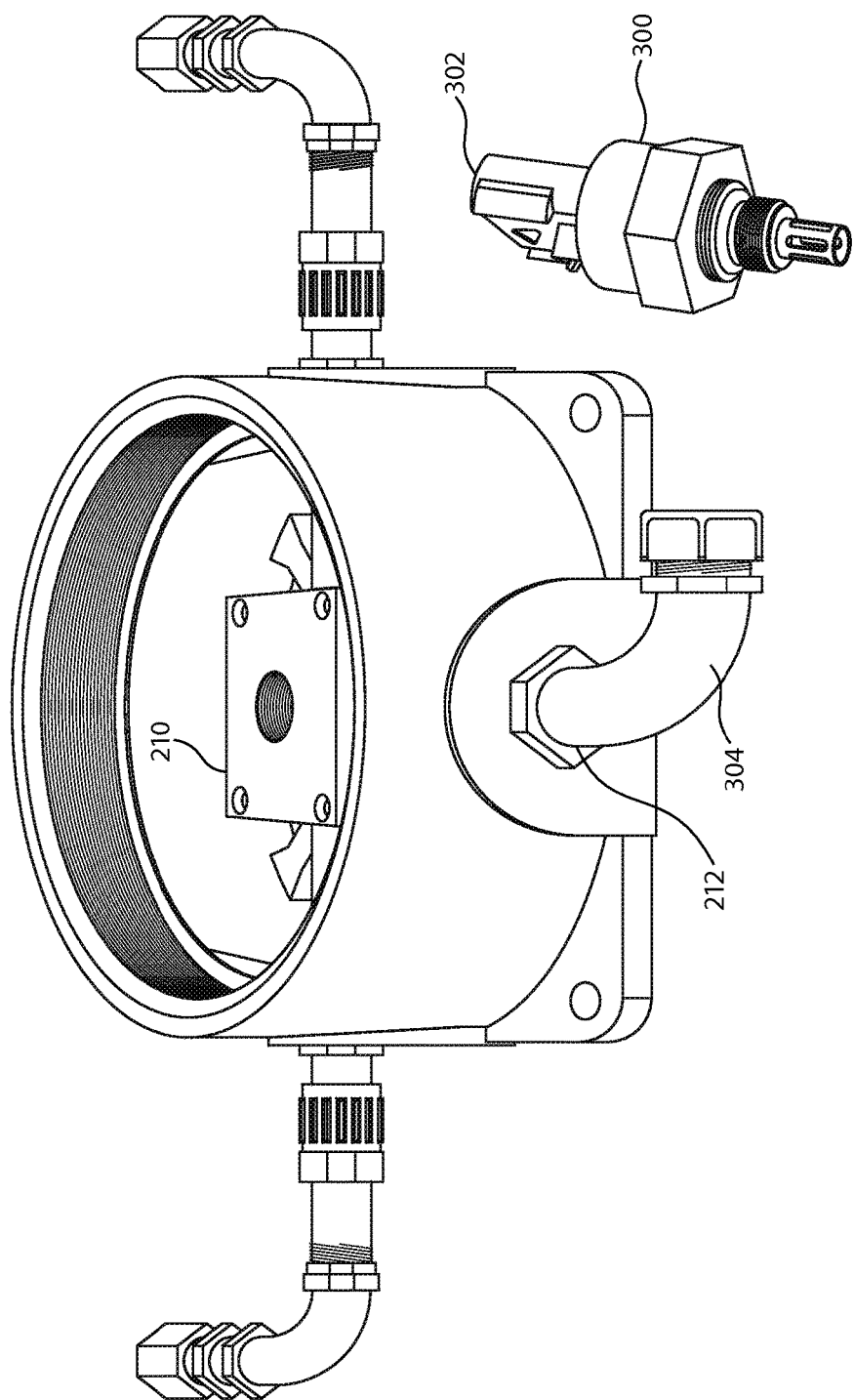
FIG. 5 includes a side perspective view of a ruggedized housing without a top or sensor in accordance with an embodiment.

Referring to FIGS. 4 and 5, in an embodiment, the sensor 300 can be removeably engaged with a multiport component 210. The multiport component 210 can be coupled to an inner surface of the body 202 of the ruggedized housing 200. The multiport component 210 can define an inner passageway in fluid communication with the fluid passageway 208. In such a manner, the he multiport component 210 can permit fluid communication between the sensor 300 and the fluid passageway 208.

As contemplated in embodiments described herein, the sensor 300 can be in fluid communication with the fluid passageway 208. For example, at least a portion of the sensor 300 can extend into the fluid passageway 208. In such a manner, the lubrication oil passing through the fluid passageway 208 can be measured by the sensor 300.

In a particular embodiment, an encapsulant (not illustrated) can surround at least a portion of the sensor 300. The encapsulant can include, for example, a foam, a gel, or a powder applied between at least a portion of the senor 300 and the wall 204 of the ruggedized housing 200. The encapsulant may cure around the sensor 300 to form a solid encapsulant. In an embodiment, the encapsulant may protect the sensor 300 from fluids such as water, vibration, heat, or shock.

In accordance with an embodiment, such as illustrated in FIG. 5, the sensor 300 can include a connection 302 adapted to engage a wire harness 308 (FIG. 4). As used herein, a "wire harness" refers to a cable adapted to power the sensor 300 or transmit data from the sensor to a logic element. The logic element can be adapted to analyze a signal generated by the sensor 300.

The sensor 300 can be coupled to the logic element. For example, in an embodiment, the connection 302 can threadedly engage the wire harness 308 with the sensor 300. In another embodiment, a surface of the wire harness 308 can form an interference fit with a portion of the sensor 300. In a further embodiment, such as illustrated in FIG. 5, the wire harness 308 can engage the sensor 300 by a snap fit. Alternatively, the wire harness 308 can be integrally formed with the sensor 300 or permanently attached thereto during or after manufacture. In yet another embodiment, the sensor 300 can be attached to the wire harness 308 by a multi-pin connection, or by any other suitable method for engaging electrical components.

Referring to FIGS. 2 to 5, the wire harness 308 can extend from the internal volume of the ruggedized housing 200 to an external location through an aperture 212 in the wall 204. In a particular embodiment, the aperture 212 can be sealed after the wire harness 308 is positioned therein. The aperture 212 can be sealed by a semi-solid material, such as, for example, a rubber O-ring. The aperture 212 can be sealed by a playable material allowed to cure. In yet a further embodiment, the wire harness 308 can be welded or otherwise adhered to the aperture 212. In yet an even further embodiment, the wire harness 308 can be sealed in the aperture 212 by an explosion-proof conduit seal, or a modification thereof.

The sensor 300 can be in communication, e.g., electrically coupled, to a logic element. Moreover, the sensor 300 can be coupled to at least one interface—either directly or indirectly.

Referring to FIG. 6, in a particular embodiment, a wire harness passageway 304 can extend from the ruggedized housing 200 to a ruggedized electrical box 306. The wire harness passageway 304 can comprise a central lumen extending along a length thereof. The wire harness 308 can extend through the central lumen from the sensor 300 to the ruggedized electrical box 306.

The ruggedized electrical box 306 can have a Class I, Division 1 & 2 standard rating according to UL1203 & FM3600(3615). In an embodiment, a transmission system, such as, for example, a wireless router or a satellite system, can be contained within the ruggedized electrical box 306. The wire harness 308 can be electrically coupled to the transmission system. The wire harness 308 can deliver a signal containing the measured condition of the lubrication oil to the transmission system. In a further embodiment, the transmission system can deliver the signal to a logic element. The logic element can analyze the signal and generate analyzed data. The analyzed data can be relayed to an interface, such as, for example, a user interface. An operator can then monitor the condition of the lubrication oil within the equipment. In another embodiment, the wire hardness 308 can transmit the signal from the sensor 300 to a logic element disposed within the ruggedized electrical box 306.

Many different aspects and embodiments are possible. Some of those aspects and embodiments are described below. After reading this specification, skilled artisans will appreciate that those aspects and embodiments are only illustrative and do not limit the scope of the present invention. Embodiments may be in accordance with any one or more of the items as listed below.

Item 1. A device for a drill rig comprising:
a ruggedized housing; and
a sensor contained in the ruggedized housing, the sensor adapted to measure at least one condition of a lubrication oil of an equipment on the drill rig.

Item 2. A ruggedized housing having a Class I, Division 1 & 2 standard rating according to UL1203 & FM3600 (3615), wherein the ruggedized housing is adapted to contain a sensor adapted to measure at least one condition of a lubrication oil of an equipment on a drill rig.

Item 3. The device or ruggedized housing according to any one of the preceding items, wherein the device further comprises:
a fluid passageway extending at least partially through an internal volume of the ruggedized housing, the fluid passageway adapted to transport the lubrication oil to the sensor.

Item 4. The device or ruggedized housing according to item 3, wherein the fluid passageway extends through the internal volume of the ruggedized housing between diametrically opposite locations.

Item 5. The device or ruggedized housing according to any one of items 3 and 4, wherein the fluid passageway extends entirely through a wall of the ruggedized housing at one or more locations.

Item 6. The device or ruggedized housing according to item 5, wherein the fluid passageway extends through the wall of the ruggedized housing at two locations.

Item 7. The device or ruggedized housing according to item 6, wherein the fluid passageway extends through the wall of the ruggedized housing at diametrically opposite locations.

Item 8. The device or ruggedized housing according to any one of items 3-7, wherein the fluid passageway extends through the internal volume along a substantially linear pathway.

Item 9. The device or ruggedized housing according to any one of items 3-8, wherein the fluid passageway extends through the internal volume along a straight line.

Item 10. The device or ruggedized housing according to any one of items 3-9, wherein a first distal end of the fluid passageway includes an engagement element adapted to engage an inlet line extending from the equipment, and wherein a second distal end of the fluid passageway includes an engagement element adapted to engage an outlet line extending from the equipment.

Item 11. The device or ruggedized housing according to any one of items 3-10, wherein the sensor is in fluid communication with the fluid passageway.

Item 12. The device or ruggedized housing according to any one of items 3-11, wherein at least a portion of the sensor extends into the fluid passageway.

Item 13. The device or ruggedized housing according to any one of items 3-12, wherein the sensor is adapted to receive unfiltered lubrication oil.

Item 14. The device or ruggedized housing according to any one of the preceding items, wherein the sensor is adapted to sense:
- a viscosity of the lubrication oil;
- a density of the lubrication oil;
- a dielectric constant of the lubrication oil;
- a temperature of the lubrication oil; or
- a combination thereof.

Item 15. The device or ruggedized housing according to any one of the preceding items, wherein the lubrication oil is a heavy weight lubrication oil.

Item 16. The device or ruggedized housing according to any one of the preceding items, wherein the lubrication oil has a weight, as measured according to the Society of Automotive Engineers (SAE), of at least 75 W, such as at least 80 W, at least 85 W, at least 90 W, at least 140 W, or even at least 250 W.

Item 17. The device or ruggedized housing according to any one of the preceding items, further comprising:
- a wire harness extending from the sensor to a location external to the ruggedized housing.

Item 18. The device or ruggedized housing according to item 17, further comprising:
- a ruggedized electrical box; and
  - a wire harness passageway extending from the ruggedized housing to the ruggedized electrical box,
  - wherein the wire harness is disposed within the wire harness passageway.

Item 19. The device or ruggedized housing according to any one of items 17 and 18, wherein the wire harness is adapted to deliver a signal from the sensor to a transmission system.

Item 20. The device or ruggedized housing according to item 19, wherein the transmission system is disposed within the ruggedized electrical box.

Item 21. The device or ruggedized housing according to any one of the preceding items, wherein the sensor is coupled to a logic element, and wherein the logic element is adapted to analyze a signal generated by the sensor.

Item 22. The device or ruggedized housing according to any one of the preceding items, wherein the sensor is coupled to at least one interface.

Item 23. The device or ruggedized housing according to item 22, wherein the sensor is adapted to deliver a signal to the interface, and wherein the signal includes information on the condition of the lubrication oil.

Item 24. The device or ruggedized housing according to any one of items 22 and 23, wherein the interface comprises a user interface.

Item 25. The device or ruggedized housing according to any one of items 22-24, wherein the signal is at least partially transferred to the interface via a transmission system.

Item 26. The device, combination, or ruggedized housing according to any one of items 22-25, wherein the signal is at least partially transmitted via a satellite system.

Item 27. The device or ruggedized housing according to any one of the preceding items, wherein the ruggedized housing comprises a split body including a first component and a second component, wherein the first component is removeably engageable with the second component, and wherein the sensor is disposed within an internal volume between the first and second components.

Item 28. The device or ruggedized housing according to any one of the preceding items, wherein the sensor is adapted to sense the condition of the lubrication oil at least 1 time per hour (TPH), such as at least 2 TPH, at least 6 TPH, at least 30 TPH, or even at least 60 TPH.

Item 29. The device or ruggedized housing according to any one of the preceding items, wherein the sensor is adapted to sense the condition of the lubrication oil no greater than 18,000 times per hour (TPH), such as no greater than 3,600 TPH, no greater than 360 TPH, or even no greater than 120 TPH.

Item 30. The device or ruggedized housing according to any one of the preceding items, wherein the equipment includes at least one of a top drive, a draw works, an engine, or a transmission positioned on a drill rig.

Item 31. The device or ruggedized housing according to any one of the preceding items, wherein a dampening element is disposed between the ruggedized housing and the equipment of the drill rig.

Item 32. The device or ruggedized housing according to any one of the preceding items, further comprising an encapsulant disposed within the internal volume of the ruggedized housing, the encapsulant occupying a vacant space of the internal volume.

Item 33. The device or ruggedized housing according to any one of the preceding items, wherein the housing is adapted to permit the sensor to withstand at least 1 g-force, such as at least 5 g-force, at least 10 g-force, at least 25 g-force, at least 50 g-force, or even at least 75 g-force.

Item 34. The device or ruggedized housing according to any one of the preceding items, wherein the ruggedized housing has a Class I, Division 1 & 2 standard rating according to UL1203 & FM3600(3615).

Item 35. A method for monitoring a lubrication oil of an equipment on a drill rig, comprising:
- providing a ruggedized housing having a Class I, Division 1 & 2 standard rating according to UL1203 & FM3600 (3615);
- providing a sensor adapted to measure at least one condition of the lubrication oil; and
- attaching the sensor and ruggedized housing to a fluid passageway adapted to contain a lubrication oil from the equipment,
- wherein the sensor is disposed within an internal volume of the ruggedized housing.

Item 36. The method according to item 35, wherein the step of attaching the sensor and ruggedized housing to the fluid passageway is performed by:
- attaching the sensor to the ruggedized housing; and
- attaching the ruggedized housing to the fluid passageway.

Item 37. The method according to any one of items 35 and 36, wherein the sensor is adapted to receive unfiltered lubrication oil.

Item 38. The method according to any one of items 35-37, further comprising:
- attaching a wire harness to the sensor; and
- extending the wire harness through a wall of the ruggedized housing,
- wherein the wire harness is adapted to deliver a signal from the sensor to a logic element, and wherein the signal includes information on the condition of the lubrication oil.

Item 39. The method according to item 38, wherein the wire harness extends to a transmission system adapted to deliver the condition to the interface.

Note that not all of the features described above are required, that a portion of a specific feature may not be required, and that one or more features may be provided in addition to those described. Still further, the order in which features are described is not necessarily the order in which the features are installed.

Certain features are, for clarity, described herein in the context of separate embodiments, may also be provided in combination in a single embodiment. Conversely, various features that are, for brevity, described in the context of a single embodiment, may also be provided separately or in any subcombinations.

Benefits, other advantages, and solutions to problems have been described above with regard to specific embodiments, However, the benefits, advantages, solutions to problems, and any feature(s) that may cause any benefit, advantage, or solution to occur or become more pronounced are not to be construed as a critical, required, or essential feature of any or all the claims.

The specification and illustrations of the embodiments described herein are intended to provide a general understanding of the structure of the various embodiments. The specification and illustrations are not intended to serve as an exhaustive and comprehensive description of all of the elements and features of apparatus and systems that use the structures or methods described herein. Separate embodiments may also be provided in combination in a single embodiment, and conversely, various features that are, for brevity, described in the context of a single embodiment, may also be provided separately or in any subcombination. Further, reference to values stated in ranges includes each and every value within that range. Many other embodiments may be apparent to skilled artisans only after reading this specification. Other embodiments may be used and derived from the disclosure, such that a structural substitution, logical substitution, or any change may be made without departing from the scope of the disclosure. Accordingly, the disclosure is to be regarded as illustrative rather than restrictive.

What is claimed is:

1. A device for a drill rig comprising:
    a ruggedized housing comprising a first component and a second component threadably engageable with one another to define an internal volume;
    a sensor contained in the internal volume, wherein the sensor is adapted to measure at least one condition of a lubrication oil of an equipment on the drill rig, the at least one condition selected from a viscosity, a density, a dielectric constant, or any combination thereof of the lubrication oil; and
    a fluid passageway extending at least partially through an internal volume of the ruggedized housing, the fluid passageway adapted to transport the lubrication oil to the sensor, wherein a first distal end of the fluid passageway includes an engagement element adapted to engage an inlet line extending from the equipment, and wherein a second distal end of the fluid passageway includes an engagement element adapted to engage an outlet line extending from the equipment.

2. The device according to claim 1, wherein the fluid passageway extends entirely through a wall of the ruggedized housing at one or more locations.

3. The device according to claim 1, wherein the sensor is adapted to sense:
    a viscosity of the lubrication oil;
    a density of the lubrication oil;
    a dielectric constant of the lubrication oil;
    a temperature of the lubrication oil; or
    a combination thereof.

4. The device according to claim 1, further comprising:
    a wire harness extending from the sensor to a location external to the ruggedized housing.

5. The device according to claim 1, further comprising an encapsulant disposed within the internal volume of the ruggedized housing, the encapsulant occupying a vacant space of the internal volume.

6. The device according to claim 1, wherein the housing is adapted to permit the sensor to withstand at least 1 g-force.

7. The device according to claim 1, wherein the lubrication oil is a heavy weight lubrication oil.

8. The device according to claim 1, wherein a dampening element is disposed between the ruggedized housing and the equipment of the drill rig.

9. The device according to claim 1, wherein the ruggedized housing has a Class I, Division 1 & 2 standard rating according to UL1203 & FM3600(3615).

10. The device of claim 1, further comprising a dampening element disposed between the ruggedized housing and the equipment of the drill rig.

11. A ruggedized housing having a Class I, Division 1 & 2 standard rating according to UL1203 & FM3600(3615), wherein the ruggedized housing contains a sensor adapted to measure at least one condition of a lubrication oil of an equipment on a drill rig, wherein a dampening element is disposed between the ruggedized housing and the equipment of the drill rig, wherein the dampening element comprises a polymeric material and has a thickness of at least 0.1 cm and not greater than 10 cm, wherein the ruggedized housing comprises a split body including a first component and a second component threadably engageable with one another.

12. The ruggedized housing according to claim 11, wherein the device further comprises:
    a fluid passageway extending at least partially through an internal volume of the ruggedized housing, the fluid passageway adapted to transport the lubrication oil to the sensor.

13. The ruggedized housing according claim 12, wherein a first distal end of the fluid passageway includes an engagement element adapted to engage an inlet line extending from the equipment, and wherein a second distal end of the fluid passageway includes an engagement element adapted to engage an outlet line extending from the equipment.

14. The ruggedized housing according to claim 11, wherein the sensor is disposed within an internal volume between the first and second components.

15. The ruggedized housing according to claim 11, further comprising an encapsulant disposed within the internal volume of the ruggedized housing, the encapsulant occupying a vacant space of the internal volume.

16. The ruggedized housing according to claim 11, wherein the housing is adapted to permit the sensor to withstand at least 1 g-force.

17. The ruggedized housing of claim 11, further comprising an aperture adapted to receive a wiring harness extending from the sensor to an external location of the ruggedized housing.

18. A method for monitoring a lubrication oil of an equipment on a drill rig, comprising:
    providing a ruggedized housing having a Class I, Division 1 & 2 standard rating according to UL1203 & FM3600 (3615), wherein the ruggedized housing comprises a first component and a second component threadably engageable with one another to define an internal volume;
    providing a sensor adapted to measure at least one condition of the lubrication oil; and attaching the sensor and ruggedized housing to a fluid passageway adapted to contain a lubrication oil from the equipment, wherein the sensor is disposed within the internal volume of the ruggedized housing comprising a fluid passageway extending at least partially through the internal volume of the ruggedized housing, the fluid passageway adapted to transport the lubrication oil to the sensor, wherein a first distal end of the fluid passageway includes an engagement element adapted to engage an inlet line extending from the equipment, and wherein a second distal end of the fluid passageway includes an engagement element adapted to engage an outlet line extending from the equipment.

19. The method of claim 18, wherein the ruggedized housing is adapted to receive a curable material comprising a foam, a gel, or a powder cured around the sensor.

20. The ruggedized housing of claim 18, further comprising an aperture adapted to receive a wiring harness extending from the sensor to an external location of the ruggedized housing.

* * * * *